(12) United States Patent
Inufusa (10) Patent No.: US 9,089,548 B2
(45) Date of Patent: Jul. 28, 2015

(54) COMPOSITION FOR PROTECTION AGAINST CELL-DAMAGING EFFECTS

(71) Applicant: TIMA FOUNDATION, Balzers (LI)

(72) Inventor: Haruhiko Inufusa, Osaka (JP)

(73) Assignee: Tima Foundation, Balzers (LI)

( * ) Notice: Subject to any disclaimer, the term of this patent is extended or adjusted under 35 U.S.C. 154(b) by 0 days.

(21) Appl. No.: 14/358,365

(22) PCT Filed: Nov. 15, 2012

(86) PCT No.: PCT/EP2012/072790
§ 371 (c)(1),
(2) Date: May 15, 2014

(87) PCT Pub. No.: WO2013/072441
PCT Pub. Date: May 23, 2013

(65) Prior Publication Data
US 2014/0314731 A1    Oct. 23, 2014

(30) Foreign Application Priority Data

Nov. 15, 2011   (EP) .................................... 11189191
Mar. 9, 2012    (EP) .................................... 12158739

(51) Int. Cl.
| | | |
|---|---|---|
| A61K 31/375 | (2006.01) | |
| A61K 31/122 | (2006.01) | |
| A61K 31/198 | (2006.01) | |
| A61K 31/455 | (2006.01) | |
| A61K 31/194 | (2006.01) | |
| A61K 31/525 | (2006.01) | |
| A23L 1/302 | (2006.01) | |
| A23L 1/305 | (2006.01) | |
| A23L 1/30 | (2006.01) | |
| A61K 31/519 | (2006.01) | |

(52) U.S. Cl.
CPC ................ *A61K 31/375* (2013.01); *A23L 1/30* (2013.01); *A23L 1/302* (2013.01); *A23L 1/3051* (2013.01); *A61K 31/122* (2013.01); *A61K 31/194* (2013.01); *A61K 31/198* (2013.01); *A61K 31/455* (2013.01); *A61K 31/519* (2013.01); *A61K 31/525* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,006,219 A | | 2/1977 | Upham et al. |
| 8,633,192 B2 * | | 1/2014 | Matuschka-Greiffenclau et al. ............ 514/251 |
| 2002/0155163 A1 | | 10/2002 | Benjamin et al. |
| 2005/0238638 A1 | | 10/2005 | Gutwein |
| 2005/0271754 A1 | | 12/2005 | Cochrane |
| 2008/0161318 A1 * | | 7/2008 | Matuschka-Greiffenclau et al. ............ 514/251 |
| 2009/0054351 A1 * | | 2/2009 | Matuschka-Greiffenclau 514/23 |
| 2011/0178048 A1 * | | 7/2011 | Repka et al. .................. 514/171 |
| 2012/0122812 A1 * | | 5/2012 | Derkach et al. ................ 514/54 |
| 2014/0086894 A1 * | | 3/2014 | Matuschka-Greiffenclau et al. ............ 424/94.1 |

FOREIGN PATENT DOCUMENTS

| | | |
|---|---|---|
| EP | 2 057 905 | 5/2009 |
| WO | WO 00/53176 | 9/2000 |
| WO | WO 03/006073 | 1/2003 |
| WO | WO 2005/077464 | 8/2005 |
| WO | WO 2005/117924 | 12/2005 |
| WO | WO 2007/016949 | 2/2007 |
| WO | WO 2007/016950 | 2/2007 |
| WO | WO 2007/017139 | 2/2007 |
| WO | WO 2008/071790 | 6/2008 |
| WO | WO 2010138095 A1 * | 12/2010 |
| WO | WO 2012/095509 | 7/2012 |

OTHER PUBLICATIONS

"Ascorbic acid (vitamin c)", from Yahoo! Health, downloaded from http://health.yahoo.com/addiction-resources/ascorbic-acid-vitamin-c/healthwise, downloaded on Jul. 3, 2009.
DiMauro et al., "Approaches to the treatment of mitochondrial diseases", *Muscle Nerve*, 34: S. 265-283, 2006.
Grundy et al., "Efficacy, safety, and tolerability of once-daily niacin for the treatment of dyslipidemia associated with type 2 diabetes: results of the assessment of diabetes control and evaluation of the efficacy of niaspan trial", *Arch Intern Med.*, 162: S. 1568-1576, 2002.
Hirsch, "Editorial: in-patient hyperglycemia—are we ready to treat it yet?", *J Clin Endocrinol Metab.*, 87(8):975-977, 2002.

(Continued)

*Primary Examiner* — Allison Fox
*Assistant Examiner* — Susan E Fernandez
(74) *Attorney, Agent, or Firm* — Parker Highlander PLLC (57) ABSTRACT

The present invention relates to a composition consisting of Vitamin C, L-glutamine, L-cystine or L-cysteine, riboflavin, succinic acid, fumaric acid, coenzyme Q10, and niacin. The present invention relates further to the use of the composition for minimizing the cell-damaging effect of radicals and harmful forms of oxygen, in particular of oxygen radicals or reactive oxygen species. The present invention relates to a composition comprising Vitamin C, L-glutamine, L-cystine or L-cysteine, riboflavin, succinic acid, fumaric acid, coenzyme Q10, and niacin, wherein the composition is administered in a concentration ranging from 10 to 20 mg/kg body weight. The present invention relates further to the composition for use in the treatment and/or prevention of radical and harmful forms of oxygen derived diseases, in particular of oxygen radical or reactive oxygen species derived diseases. The present invention relates further to the composition as a food supplement or dietary supplement.

8 Claims, 4 Drawing Sheets

(56) References Cited

OTHER PUBLICATIONS

Ihara et al., "Antioxidant α-tocopherol ameliorates glycemic control of GK rats, a model of type 2 diabetes", *FEBS Letters*, 473:24-26, 2000.

Opara, "Role of oxidative stress in the etiology of type 2 diabetes and the effect of antioxidant supplementation on glycemic control", *Journal of Investigative Medicine*, 52(1):19-23, 2004.

PCT International Preliminary Report on Patentability, issued in International Application No. PCT/EP2012/072790, mailed Apr. 2, 2014.

PCT International Search Report and Written Opinion of the International Searching Authority, issued in International Application No. PCT/EP2012/072790, mailed Feb. 20, 2013.

PCT Supplemental Written Opinion of the International Preliminary Examining Authority, issued in International Application No. PCT/EP2012/072790, mailed Feb. 14, 2014.

PCT Written Opinion of the International Preliminary Examining Authority, issued in International Application No. PCT/EP2012/072790, mailed Nov. 12, 2013.

\* cited by examiner

COMPOSITION FOR PROTECTION AGAINST CELL-DAMAGING EFFECTS

This application is a national phase application under 35 U.S.C. §371 of International Application No. PCT/EP2012/072790, filed Nov. 15, 2012, which claims priority to European Application No. 11189191.7, filed Nov. 15, 2011, and European Application No. 12158739.8, filed Mar. 9, 2012. The entire text of each of the above referenced disclosures is specifically incorporated herein by reference.

The present invention relates to a composition consisting of Vitamin C, L-glutamine, L-cystine or L-cysteine, riboflavin, succinic acid, fumaric acid, coenzyme Q10, and niacin. The present invention relates further to the use of the composition for minimizing the cell-damaging effect of radicals and harmful forms of oxygen, in particular of oxygen radicals or reactive oxygen species. The present invention relates to a composition comprising Vitamin C, L-glutamine, L-cystine or L-cysteine, riboflavin, succinic acid, fumaric acid, coenzyme Q10, and niacin, wherein the composition is administered in a concentration ranging from 10 to 20 mg/kg body weight. The present invention relates further to the composition for use in the treatment and/or prevention of radical and harmful forms of oxygen derived diseases, in particular of oxygen radical or reactive oxygen species derived diseases. The present invention relates further to the composition as a food supplement or dietary supplement.

Though oxygen is absolutely required for aerobic life, it can participate in a variety of toxic reactions involving oxygen free radicals and transition metals that damage many biomolecules. In the past, the oxidative damage of a great number of many low-molecular and macromolecular compounds and fluids of biological and technical interest has been investigated by several approaches. The damaging effects were induced by Reactive Oxygen Species (ROS), obtained by radiolysis of water caused e.g. by ionizing radiation such as X- or gamma-radiation or by metal-catalyzed cleavage of hydrogen peroxide ($H_2O_2$). Among the physicochemical techniques, in particular spectroscopic studies of many biomolecules revealed, effectively and very fast, numerous changes of the local and global structure of the constituents, together with alterations of their functional ability.

Free radicals are highly reactive owing to the presence of unpaired electron(s). Radicals are short-lived; however they attack, effectively and very fast, all other molecules located close to them. Such so-called primary effects occur in sub-seconds. However, because of chain propagation processes, radicals may also cause damage far in excess of their original reaction products and far away from their initial place of formation. A cascade of uncontrollable reactions will take place after their attack. Such secondary effects occur in seconds to years. Although $H_2O_2$ belongs to the ROS group it is no radical, i.e. it is less dangerous, but has more time to react and is responsible for many additional secondary effects.

In the case of ROS-treated or irradiated air-saturated aqueous solutions, the most important noxious species involved in the primary damages of biomolecules are hydroxyl radicals (.OH), and to a minor extent superoxide anion radicals ($O_2.^-$) and hydrogen peroxide ($H_2O_2$). Hydroxyl radicals (.OH) are considered to be responsible for the most deleterious, primary effects on biomolecules and for the damages within the body. Consequently, substances which act as strong .OH scavengers are most effective in avoiding noxious effects of ionizing radiation, in particular when present in high concentrations. $H_2O_2$ is responsible for many secondary effects, since it is stable for some time.

Addition of certain compounds to the samples prior to treatment/irradiation (a.r. (ante radiationem i.e. before irradiation) additives) or afterwards (p.r. (post radiationem i.e. after irradiation) additives) unveiled a great number of possible modifications of the occurring damages. These substances may be used for testing the extent of protection and reparability. Modifications of the effects, however, may also be achieved by changes of other environmental conditions such as the type of ROS production or the wavelength of the radiation applied.

In vivo, ROS effects and oxidative damage are suppressed largely by efficient antioxidant defense mechanisms; these defense systems, however, can only work if sufficient amounts of bioprotectives, e.g. scavengers, antioxidants and antioxienzymes are available. Otherwise serious, frequently irreversible damages of biomolecules may occur.

As a consequence of the scavenging process, scavengers themselves are destroyed or at least transformed to compounds which are incapable of further acting as scavengers. The simultaneous presence of putative scavengers in solution may lead to quite different effects, e.g. synergism, additivity, prevalence of one effective scavenger, weakening of the effect of the prevalent scavenger, no effect, or even effects more detrimental than in the absence of any scavenger. Some substances can act as either anti-oxidants or pro-oxidants (some kind of 'radical reversal'), depending on the specific set conditions, e.g. concentration, presence of oxygen or transition metals. In general, higher concentrations of scavengers amplify the protective effects. In some cases, however, the given conditions may lead to antagonistic effects, thereby reducing positive effects. The presence of the enzyme catalase or peroxidase can decompose $H_2O_2$, thereby impeding the long-term effects of this agent.

Since the naturally occurring defence system of the body is able to combat only certain, rather moderate amounts of ROS (usually occurring in the body), an excess of ROS can only be met by supply of selected additives, preferably antioxidants. This is necessarily the case when high levels of oxidative stress are reached. Otherwise an imbalance between the production and manifestation of ROS and the ability to detoxify the reactive intermediates or to repair the resulting damage will occur. This imbalance may contribute to the aging process and may lead to many human diseases, including heart disease and cancer.

Thus, there is a need for new compositions that are effective against radicals and harmful forms of oxygen.

This object is solved by the subject matter defined in the claims.

The following figures illustrate the present invention.

FIG. 3 shows a column diagram representing the concentration of hydrogen peroxide in the blood of mice. The negative control presents the concentration of hydrogen peroxide in the blood of mice which were untreated. The positive control presents the concentration of hydrogen peroxide in the blood of mice which were irradiated by using radiation doses of 6 Gy and blood sampling was performed 72 hours after irradiation. The Vit.C 150 mg/kg data, Vit.C 15 mg/kg data and composition 15 mg/kg data represent the concentration of hydrogen peroxide in the blood of mice treated three times in a 24 hours interval with 150 mg/kg Vitamin C, 15 mg/kg Vitamin C and 15 mg/kg composition of Example 6, respectively. 24 hours after administration the mice were irradiated with a radiation dose of 6 Gy and 72 hours after irradiation blood sampling was performed. The hydrogen peroxide concentration was measured with the Free Carpe Diem photometric analysis system (Diacron, Grosseto, Italy). Abbreviations: Vit.C: Vitamin C; Composition: composition as described in Example 6.

FIG. 4 shows a column diagram representing the concentration of hydrogen peroxide in the blood of mice. The negative control presents the concentration of hydrogen peroxide in the blood of mice which were untreated. The positive control presents the concentration of hydrogen peroxide in the blood of mice which were irradiated by using radiation doses of 6 Gy and blood sampling was performed 72 hours after irradiation. The single data represent the concentration of hydrogen peroxide in the blood of mice treated three times in a 24 hours interval with 5, 10, 15, 20, 25 or 30 mg/kg composition of Example 8, respectively. 24 hours after oral administration the mice were irradiated with a radiation dose of 6 Gy and 72 hours after irradiation blood sampling was performed. The hydrogen peroxide concentration was measured with the Free Carpe Diem photometric analysis system (Diacron, Grosseto, Italy).

FIG. 5 shows a column diagram representing the concentration of hydrogen peroxide in the blood of mice. The 6 Gy Radiation data presents the concentration of hydrogen peroxide in the blood of mice which were irradiated by using radiation doses of 6 Gy and blood sampling was performed 72 hours after irradiation. The 3 days pre-treat data represents the concentration of hydrogen peroxide in the blood of mice treated three times in a 24 hours interval with 15 mg/kg composition of Example 8 before irradiation 24 hours after last oral administration and blood sampling was performed 72 hours after irradiation. The 4 days post-treat data represents the concentration of hydrogen peroxide in the blood of mice treated four times in a 24 hours interval with 15 mg/kg composition of Example 8 starting 24 hours after irradiation and blood sampling was performed 24 hours after last oral administration. The 7 days (3 pre+4 post) data represents the concentration of hydrogen peroxide in the blood of mice treated three times in a 24 hours interval with 15 mg/kg composition of Example 8 before irradiation and four times in a 24 hours interval starting 24 hours after irradiation and blood sampling was performed 24 hours after last oral administration. The 3 days pre-treat, cysteine version data represents the concentration of hydrogen peroxide in the blood of mice treated three times in a 24 hours interval with 15 mg/kg composition of Example 8, wherein cystine is replaced by cysteine, before irradiation 24 hours after last oral administration and blood sampling was performed 72 hours after irradiation. The 3 days pre-treat, intra-peritoneal data represents the concentration of hydrogen peroxide in the blood of mice treated three times in a 24 hours interval with 15 mg/kg composition of Example 8, wherein the composition was administered intra-peritoneal, before irradiation 24 hours after last administration and blood sampling was performed 72 hours after irradiation. The irradiation was performed by using radiation doses of 6 Gy. The hydrogen peroxide concentration was measured with the Free Carpe Diem photometric analysis system (Diacron, Grosseto, Italy).

FIG. 6 shows a column diagram representing the concentration of hydrogen peroxide in the blood of mice. The negative control presents the concentration of hydrogen peroxide in the blood of mice which were untreated. The positive control presents the concentration of hydrogen peroxide in the blood of mice to which 7 g/kg body weight ethanol was administrated twice intra-peritoneal in a 24 hours interval and 24 hours after the second administration blood sampling was performed. The single data represent the concentration of hydrogen peroxide in the blood of mice treated five times in a 24 hours interval with 10, 15, 20, 25 or 30 mg/kg composition of Example 8, respectively. 7 g/kg body weight ethanol was injected intra-peritoneal on day 4 and 5 one hour after the treatment with the composition of Example 8. 24 hours after final treatment with composition of Example 8 blood sampling was performed. The hydrogen peroxide concentration was measured with the Free Carpe Diem photometric analysis system (Diacron, Grosseto, Italy).

Figure 1:
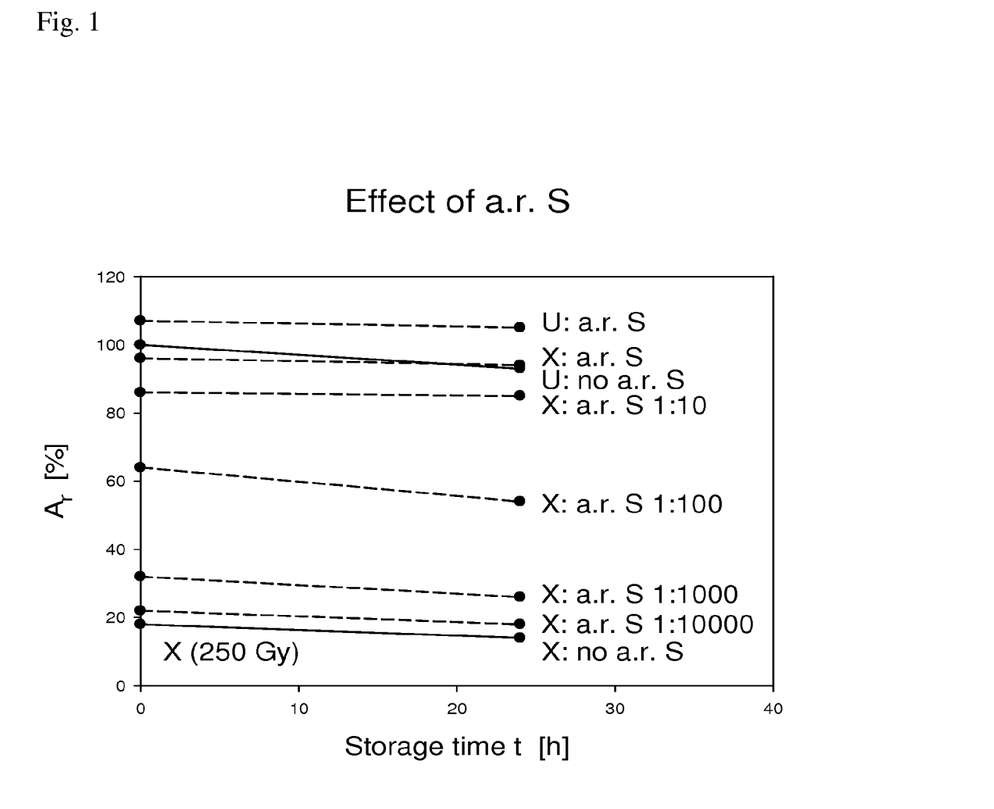
FIG. 1 shows in a graphical representation the residual activity ($A_r$) of unirradiated (U) and X-irradiated (X) lysozyme (c=0.1 mg/ml) in the post-irradiation phase in the absence or presence of the composition according to the invention before the exposure to radiation. The irradiation of the lysozyme was performed using X-ray doses of 250 Gy. The gray (Gy), with units J/kg, is the SI unit of absorbed dose, which represents the amount of radiation required to deposit 1 joule of energy in 1 kilogram of any kind of matter. Abbreviations: a.r.: ante radiationem i.e. before irradiation; S: composition as described in Example 1.
Figure 2:
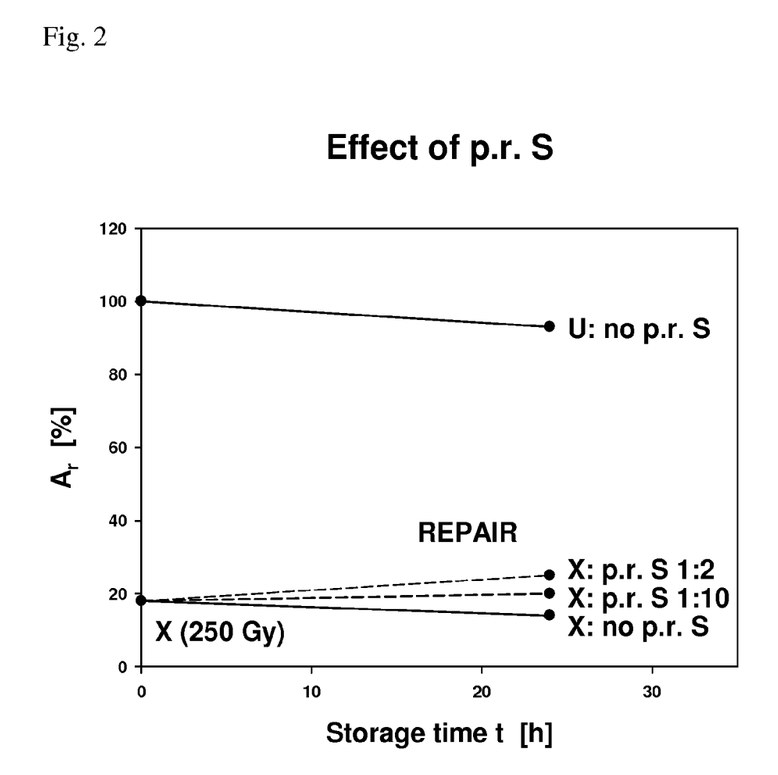
FIG. 2 shows in a graphical representation the residual activity ($A_r$) of unirradiated (U) and X-irradiated (X) lysozyme (c=0.1 mg/ml) in the post-irradiation phase in the absence or presence of composition according to the invention after the exposure to radiation. The irradiation of the lysozyme was performed using X-ray doses of 250 Gy. The gray (Gy), with units J/kg, is the SI unit of absorbed dose, which represents the amount of radiation required to deposit 1 joule of energy in 1 kilogram of any kind of matter. Abbreviations: p.r.: post radiationem i.e. after irradiation; S: composition as described in Example 1.
Figure 3:
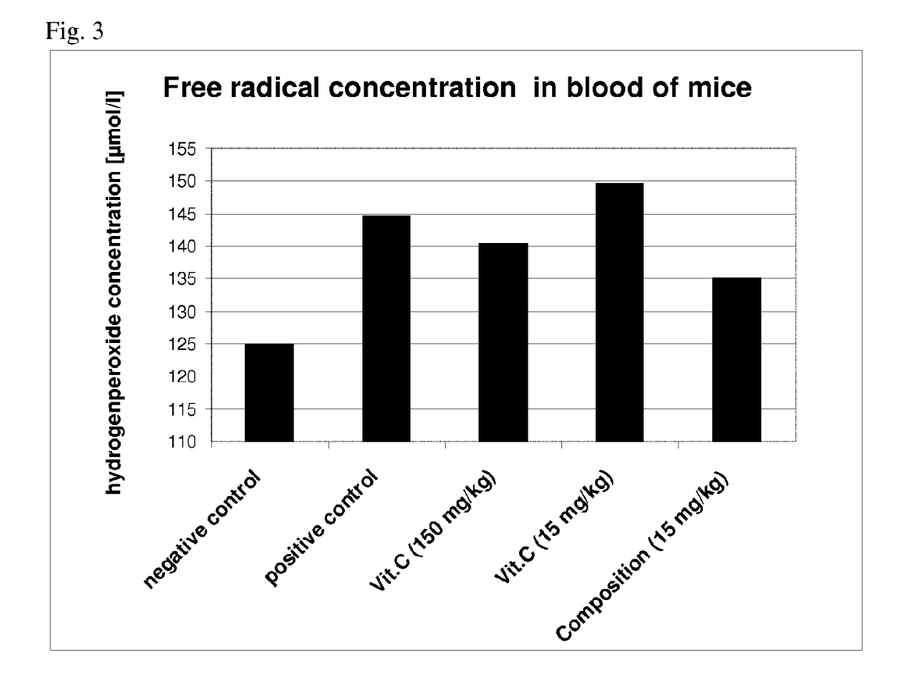
Figure 4:
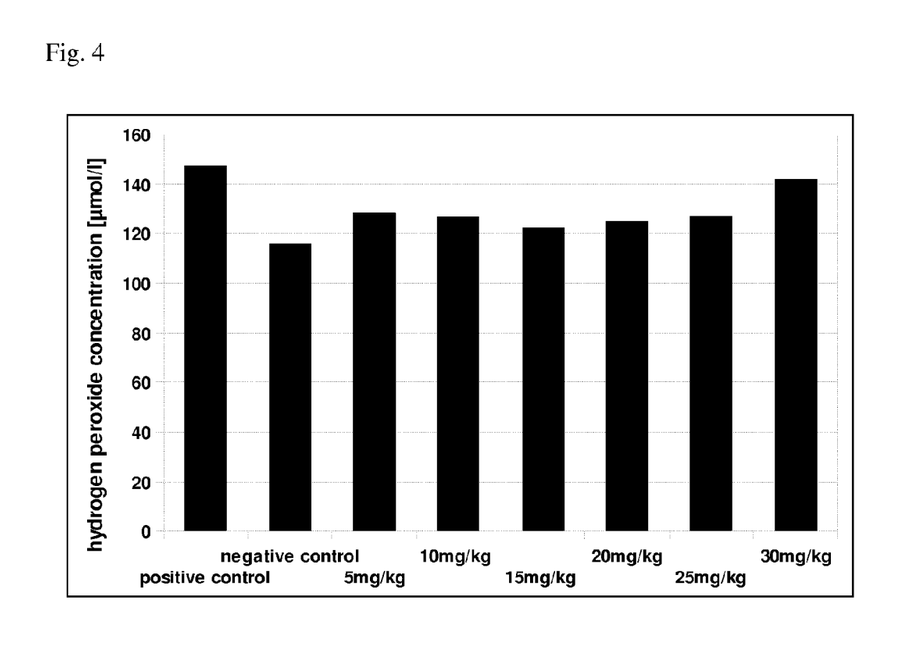
Figure 5:
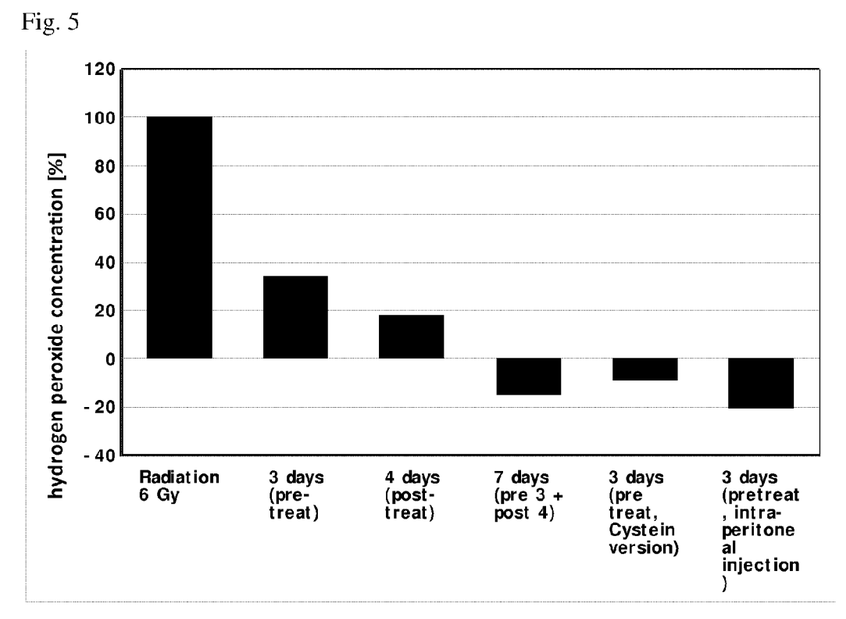
Figure 6:
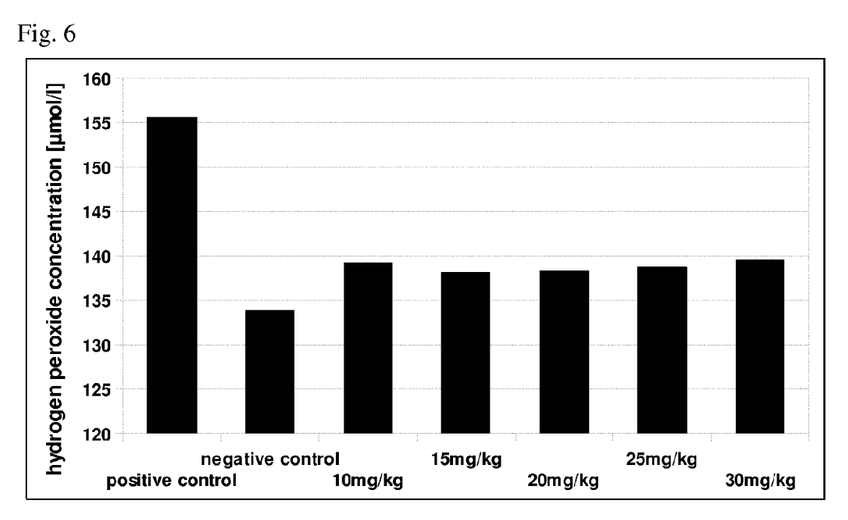

The term "composition" as used herein, refers to any kind of composition which could be applied to a subject in any form without causing toxic symptoms in the subject to which physiologically compatible amounts of the respective composition are applied.

The term "supplement", "dietary supplement" or "food supplement" as used herein, refers to a composition which is consumed in addition to the daily meals or in between.

The term "dosage form" as used herein, refers to an amount of medication to be taken at one time, optionally in regular intervals.

The term "minimizing" as used herein, refers to a reduction of the cell-damaging effect caused by radicals in all degrees, i.e. from the total avoiding of the occurrence of cell-damaging effects to the slightest improvement of the cell-damaging effects.

The term "radical" as used herein, refers to atoms, molecules or ions with at least one unpaired electron. Free radicals may have positive, negative, or zero charge. With some exceptions, the unpaired electrons cause radicals to be highly chemically reactive. Radicals containing several unpaired electrons are called diradical or biradical, triradical and so on. Radicals play an important role in specific oxidation processes, in polymerisation and in some substitution reactions. Radicals, if allowed to run free in the body, are believed to be involved in degenerative diseases, senescence (the aging process), and cancers. Radicals may be formed by heat via thermolytic cleavage, electrochemically by oxidation and reduction respectively, by X-radiation or other ionizing radiation, e.g. α-, β- and γ-radiation and by acetaldehyde or by consumption of alcohol.

The term "cell-damaging effects" as used herein, refers to the damage of biomolecules, e.g. nucleic acids, such as DNA and RNA, proteins, enzymes, amino acids, sugars, hormones and metabolites, oxidations of polyunsaturated fatty acids in lipids (lipid peroxidation), oxidations of amino acids in proteins and oxidative inactivation of specific enzymes by oxidation of co-factors.

The term "oxygen radicals" or "reactive oxygen species" as used herein, refers to substances that cause a cell damaging effect e.g. through naturally occurring free radicals or free radicals occurring through heat via thermolytic cleavage, electrochemically through oxidation and reduction respectively, and through X-radiation or other ionizing radiation, e.g. α-, β- and γ-radiation. "Oxygen radicals" or "reactive oxygen species" are both harmful forms of oxygen. Examples include superoxide radicals, hydroxyl radicals, hypochlorite radicals, hydrogen peroxide, various lipid peroxides, peroxy radical, alkoxy radical of lipids, hydroperoxide, ozone and hypochlorite anion, as well as excited oxygen molecules (singlet oxygen).

The term "radical-derived diseases" as used herein refers to a pathological condition of an individual which results at least in part from the production or exposure to free radicals, particularly oxygen radicals and other reactive oxygen species in vivo. It is evident to those of skill in the art that most pathological conditions are multifactorial, in that multiple factors contributing to the disease state are present. Such diseases encompass pathological states that are recognized in the art as being conditions wherein damage from free radicals, in particular oxygen radicals or reactive oxygen species is believed to contribute to the pathology of the disease state by increasing symptoms, decreasing survival, or providing other detectable clinical symptoms of the pathological state.

The present invention relates to a composition comprising Vitamin C, L-glutamine, L-cystine or L-cysteine, riboflavin, succinic acid, fumaric acid, coenzyme Q10, and niacin.

In a preferred embodiment the present invention relates to a composition consisting of Vitamin C, L-glutamine, L-cystine or L-cysteine, riboflavin, succinic acid, fumaric acid, coenzyme Q10, and niacin.

A standard dose comprises about 1.0 g Vitamin C, 1.0 g L-glutamine, 500 mg L-cystine or L-cysteine, 40 mg riboflavin, 100 mg succinic acid or one of its salts (e.g. succinate), 100 mg fumaric acid or one of its salts (e.g. fumarate), 100 mg coenzyme Q10 and 20 mg niacin (Vitamin B3). Preferably the relation of the components of the composition is oriented towards the above given relation. The overall dosage may be adapted to the body mass weight of the consumer.

In a preferred embodiment the standard dose of the composition of the present invention includes 100 mg coenzyme Q10, 40 mg riboflavin, 500 mg L-cystine or L-cysteine, 20 mg niacin, 940 mg Vitamin C, 100 mg succinic acid, 100 mg fumaric acid and 950 mg L-glutamine.

In another preferred embodiment the standard dose of the composition of the present invention includes 10 mg coenzyme Q10, 4 mg riboflavin, 50 mg L-cystine or L-cysteine, 2 mg niacin, 94 mg Vitamin C, 10 mg succinic acid, 10 mg fumaric acid and 85 mg L-glutamine. More preferably, the standard dose additionally comprises 20 mg cellulose, 20 mg maltose, 28.3 mg milk sugar and 6.2 mg stearic acid calcium.

In another preferred embodiment the standard dose of the composition of the present invention consists of 10 mg coenzyme Q10, 4 mg riboflavin, 50 mg L-cystine or L-cysteine, 2 mg niacin, 94 mg Vitamin C, 10 mg succinic acid, 10 mg fumaric acid, 85 mg L-glutamine, 20 mg cellulose, 20 mg maltose, 28.3 mg milk sugar and 6.2 mg stearic acid calcium.

Preferably, the relation of the composition is in a range of about 3 to 5% coenzyme Q10, 1 to 2% riboflavin, 15 to 20% L-cystine or L-cysteine, 0.5 to 1.0% niacin, 28 to 43% Vitamin C, 3 to 5% succinic acid, 3 to 5% fumaric acid and 27 to 42% L-glutamine, each in mass %. More preferably the relation of the composition is in a range of about 3.77% coenzyme Q10, 1.51% riboflavin, 18.88% L-cystine or L-cysteine, 0.75% niacin, 35.47% Vitamin C, 3.77% succinic acid, 3.77% fumaric acid and 32.08% L-glutamine, each in mass %.

In a preferred embodiment coenzyme Q10 of the composition according to the present invention is provided as CoQ10P40 (Nisshin Pharma, Tokyo, Japan) containing 40% coenzyme Q10.

It is possible to add further substances such as fruit juice extracts, curcuma, tannin, a powder of *Panax notoginseng*, and *Vinca rosea* in suitable amounts. Oolong tea, aloe vera and spiral water algae might also be added.

Preferably, the composition according to the present invention comprises a niacin fraction in a quantity ranging from and including 0.05 to 2 mg/kg body weight, 0.1 to 1.5 mg/kg body weight, 0.2 to 0.75 mg/kg body weight, 0.04 to 0.23 mg/kg body weight, 0.08 to 0.15 mg/kg body weight, 0.1 to 0.2 mg/kg body weight or 0.11 to 0.15 mg/kg body weight, preferably 0.25 mg/kg body weight, more preferably 0.11 mg/kg body weight.

Preferably, the composition according to the present invention comprises a L-cystine or L-cysteine fraction in a quantity ranging from and including 1 to 15 mg/kg body weight, 2.5 to 10 mg/kg body weight, 5 to 8 mg/kg body weight, 0.94 to 5.66 mg/kg body weight, 0.19 to 3.8 mg/kg body weight, 2.8 to 3.8 mg/kg body weight or 2.83 to 3.77 mg/kg body weight, preferably 6.25 mg/kg body weight, more preferably 2.83 mg/kg body weight.

Preferably, the composition according to the present invention comprises a L-glutamine fraction in a quantity ranging from and including 1 to 20 mg/kg body weight, 5 to 15 mg/kg body weight, 7 to 12 mg/kg body weight, 1.6 to 9.62 mg/kg body weight, 3.2 to 6.4 mg/kg body weight, 4.8 to 6.5 mg/kg body weight or 4.81 to 6.42 mg/kg body weight, preferably 11.875 mg/kg body weight, more preferably 4.81 mg/kg body weight.

Preferably, the composition according to the present invention comprises a riboflavin fraction in a quantity ranging from and including 0.05 to 2 mg/kg body weight, 0.1 to 1.5 mg/kg body weight, 0.2 to 0.75 mg/kg body weight, 0.08 to 0.45 mg/kg body weight, 0.15 to 0.3 mg/kg body weight, 0.2 to 0.3 mg/kg body weight or 0.23 to 0.3 mg/kg body weight, preferably 0.5 mg/kg body weight, more preferably 0.23 mg/kg body weight.

Preferably, the composition according to the present invention comprises a succinic acid fraction in a quantity ranging from and including 0.1 to 10 mg/kg body weight, 0.5 to 5 mg/kg body weight, 0.75 to 2 mg/kg body weight, 0.19 to 1.13 mg/kg body weight, 0.38 to 0.76 mg/kg body weight, 0.5 to 0.8 mg/kg body weight or 0.57 to 0.76 mg/kg body weight, preferably 1.25 mg/kg body weight, more preferably 0.57 mg/kg body weight.

Preferably, the composition according to the present invention comprises a fumaric acid fraction in a quantity ranging from and including 0.1 to 10 mg/kg body weight, 0.5 to 5 mg/kg body weight, 0.75 to 2 mg/kg body weight, 0.19 to 1.13 mg/kg body weight, 0.38 to 0.76 mg/kg body weight, 0.5 to 0.8 mg/kg body weight or 0.57 to 0.76 mg/kg body weight, preferably 1.25 mg/kg body weight, more preferably 0.57 mg/kg body weight.

Preferably, the composition according to the present invention comprises a coenzyme Q10 fraction in a quantity ranging from and including 0.1 to 10 mg/kg body weight, 0.5 to 5 mg/kg body weight, 0.75 to 2 mg/kg body weight, 0.19 to 1.13 mg/kg body weight, 0.38 to 0.76 mg/kg body weight, 0.5 to 0.8 mg/kg body weight or 0.57 to 0.76 mg/kg body weight, preferably 1.25 mg/kg body weight, more preferably 0.57 mg/kg body weight.

Preferably, the composition according to the present invention comprises a Vitamin C fraction in a quantity ranging from and including 1 to 20 mg/kg body weight, 5 to 15 mg/kg body weight, 7 to 12 mg/kg body weight, 3.5 to 7.1 mg/kg body weight, 5.3 to 7.1 mg/kg body weight, 5.32 to 7.09 mg/kg body weight, preferably 11.75 mg/kg body weight, more preferably 5.32 mg/kg body weight.

In a preferred embodiment the composition according to the present invention may be administered in a concentration of 5, 10, 15, 20, 25 or 30 mg/kg body weight, preferably in a concentration ranging from 5 to 30 mg/kg body weight, more preferably in a concentration ranging from 10 to 20 mg/kg body weight or 15 to 20 mg/kg body weight. In a preferred embodiment the relation of the amounts of the single components of the composition of the present invention comprises 10 mg coenzyme Q10, 4 mg riboflavin, 50 mg L-cystine or L-cysteine, 2 mg niacin, 94 mg Vitamin C, 10 mg succinic acid, 10 mg fumaric acid and 85 mg L-glutamine, i.e. in total 265 mg. In another preferred embodiment the relation of the amounts of the single components of the composition of the present invention consists of 10 mg coenzyme Q10, 4 mg riboflavin, 50 mg L-cystine or L-cysteine, 2 mg niacin, 94 mg Vitamin C, 10 mg succinic acid, 10 mg fumaric acid and 85 mg L-glutamine.

Preferably, the composition is constituted in a manner wherein a dosage of same includes a Vitamin C fraction of about 35.47 mass % i.e. a quantity of Vitamin C in the range from 0.78 to 1.18 g, preferably 1.0 g, more preferably 940 mg within a dose of 2.75 g for a person with a body weight of about 80 kg. In another preferred embodiment the composition is constituted in a manner wherein a dosage of same includes a Vitamin C fraction in the range from about 140 to 851 mg or 284 to 568 mg, preferably 425 to 567 mg, more preferably 425 mg within a dose for a person with a body weight of about 80 kg.

Preferably, the composition is constituted in a manner wherein a dosage of same includes a L-glutamine fraction of about 32.08 mass %, i.e. a quantity of said L-glutamine fraction in the range from 0.78 to 1.18 g, preferably 1.0 g, more preferably 950 mg within a dose of 2.75 g for a person with a body weight of about 80 kg. In another preferred embodiment the composition is constituted in a manner wherein a dosage of same includes a L-glutamine fraction in the range from about 128 to 770 mg or 257 to 513 mg, preferably 385 to 513 mg, more preferably 385 mg within a dose for a person with a body weight of about 80 kg.

Preferably, the composition is constituted in a manner wherein a dosage of same includes a L-cystine or L-cysteine fraction of about 18.88 mass %, i.e. a quantity of said L-cystine or L-cysteine fraction in the range from 460 to 540 mg, preferably 500 mg, within a dose of 2.75 g for a person with a body weight of about 80 kg. In another preferred embodiment the composition is constituted in a manner wherein a dosage of same includes a L-cystine or L-cysteine fraction in the range from about 76 to 453 mg or 151 to 302 mg, preferably 226 to 302 mg, more preferably 226 mg within a dose for a person with a body weight of about 80 kg.

Preferably, the composition is constituted in a manner wherein a dosage of same includes a riboflavin fraction of about 1.51 mass % i.e. a quantity of said riboflavin in the range from 32 to 48 mg, preferably 40 mg, within a dose of 2.75 g for a person with a body weight of about 80 kg. In another preferred embodiment the composition is constituted in a manner wherein a dosage of same includes a riboflavin fraction in the range from about 6 to 36 mg or 12 to 30 mg, preferably 18 to 24 mg, more preferably 18.1 mg within a dose for a person with a body weight of about 80 kg.

Preferably, the composition is constituted in a manner wherein a dosage of same includes a succinic acid fraction or one of its salts (e.g. succinate) of about 3.77 mass %, i.e. a quantity of said succinic acid in the range from 90 to 110 mg, preferably 100 mg, within a dose of 2.75 g for a person with a body weight of about 80 kg. In another preferred embodiment the composition is constituted in a manner wherein a dosage of same includes a succinic acid fraction in the range from about 15 to 91 mg or 30 to 60 mg, preferably 45 to 60 mg, more preferably 30.2 mg within a dose for a person with a body weight of about 80 kg.

Preferably, the composition is constituted in a manner wherein a dosage of same includes a fumaric acid fraction or one of its salts (e.g. fumarate) of about 3.77 mass %, i.e. a quantity of said fumaric acid in the range from 90 to 110 mg, preferably 100 mg, within a dose of 2.75 g for a person with a body weight of about 80 kg. In another preferred embodiment the composition is constituted in a manner wherein a dosage of same includes a fumaric acid fraction in the range from about 15 to 91 mg or 30 to 60 mg, preferably 45 to 60 mg, more preferably 30.2 mg within a dose for a person with a body weight of about 80 kg.

Preferably, the composition is constituted in a manner wherein a dosage of same includes a coenzyme Q10 fraction of about 3.77 mass %, i.e. a quantity of said coenzyme fraction in the range from 30 to 300 mg, preferably 250 mg, within a dose of 2.75 g for a person with a body weight of about 80 kg. In another preferred embodiment the composition is constituted in a manner wherein a dosage of same includes a succinic acid fraction in the range from about 15 to 91 mg or 30 to 60 mg, preferably 45 to 60 mg, more preferably 30.2 mg within a dose for a person with a body weight of about 80 kg.

Preferably, the composition is constituted in a manner wherein a dosage of same includes a niacin fraction of about 0.75 mass %, i.e. a quantity of said niacin fraction in the range from 1 to 40 mg, preferably 20 mg, within a dose of 2.75 g for a person with a body weight of about 80 kg. In another preferred embodiment the composition is constituted in a manner wherein a dosage of same includes a niacin fraction in the range from about 3 to 18 mg or 6 to 12 mg, preferably 9 to 12 mg or more preferably 9 mg within a dose for a person with a body weight of about 80 kg.

More preferably each ingredient of the composition is in the range from about 0.01 to about 100 gram, preferably from about 0.05 to 50 gram.

In a preferred embodiment the composition according to the invention is provided in liquid form. The composition according to the invention in liquid form may additionally comprise a buffer system for solubility reasons. Preferably the buffer system is bicarbonate, phosphate or any other buffering system. In another preferred embodiment the composition according to the invention is provided in liquid form with added bicarbonate, preferably the standard dose of the composition according to the invention comprises a sodium bicarbonate fraction ranging from and including 0.2 to 10 mg/kg body weight, 0.5 to 5 mg/kg body weight, 0.2 to 0.95 mg/kg body weight, 0.5 to 0.63 mg/kg body weight or 1 to 4 mg/kg body weight, preferably 0.95 mg/kg body weight, more preferably 0.48 mg/kg body weight. In another preferred embodiment the liquid composition according to the invention is constituted in a manner wherein a dosage of same includes a sodium bicarbonate fraction of about 2.96 mass %, i.e. a quantity of said sodium bicarbonate fraction in the range from 1 to 100 mg, preferably 84 mg, within a dose of 2.834 g for a person with a body weight of about 80 kg.

In another preferred embodiment the liquid composition according to the invention is constituted in a manner wherein a dosage of same includes a sodium bicarbonate fraction in the range from 12 to 76 mg, preferably 38 to 50.7 mg, more preferably 38 mg for a person with a body weight of about 80 kg.

In a preferred embodiment the composition according to the invention provided in liquid form comprises Vitamin C, L-glutamine, L-cystine, riboflavin, succinic acid, fumaric acid, coenzyme Q10, and niacin. More preferably, the composition according to the invention provided in liquid form comprises Vitamin C, L-glutamine, L-cystine, riboflavin, succinic acid, fumaric acid, coenzyme Q10, niacin and a buffer system for solubility reasons. Preferably the buffer system is bicarbonate, phosphate or any other buffering system.

It is possible to add further substances such as fruit juice extracts, curcuma, tannin, a powder of *Panax notoginseng*, and *Vinca rosea* in suitable amounts. Oolong tea, aloe vera and spiral water algae might also be added.

The composition according to the present invention may be administered by any route of administration, such as topical, enteral and parenteral, preferably orally.

The composition according to the present invention may be provided in form of a tablet, capsule, dragee, pill, powder, suppository, or any other galenic formulation. The tablet, capsule, dragee, pill, powder, suppository, or any other galenic formulation may be contained in a dosage receptacle. Preferably, the dosage form may comprise suitable carriers, stabilizers, flavourings, buffers or other suitable reagents, such as cellulose, maltose, milk sugar, stearic acid calcium. The standard dosage of the composition of the invention may be provided in one or more tablets, capsules, dragees, pills, powders, suppositories, or any other galenic formulations, preferably in 5 tablets, capsules, dragees, pills, powders, suppositories, or any other galenic formulations. Preferably, the composition according to the present invention is provided as a solution, emulsion or suspension. In another preferred embodiment the compounds of the composition according to the present invention are solubilized or microparticulate active agents.

The composition according to the present invention may be administered or taken prior, during or after occurrence of radicals or species of the reactive radical group, preferably oxygen radicals or reactive oxygen species or other harmful forms of oxygen. The composition according to the present invention may be taken or administered to any subject, preferably to mammals, more preferably to humans or pets or farmed animals. Pets may be for example dogs and cats, rodent pets, such as gerbils, hamsters, chinchillas, fancy rats, and guinea pigs; avian pets, such as canaries, parakeets, and parrots; reptile pets, such as turtles, lizards and snakes; and aquatic pets, such as tropical fish and frogs. Farmed animals may be for example cattle, goats, horses, rabbits, sheeps and pigs.

Another aspect of the present invention refers to the use of the composition according to the invention for minimizing the cell-damaging effects caused by radicals and harmful forms of oxygen. In a preferred embodiment the composition according to the present invention is used for minimizing the cell-damaging effects caused by harmful forms of oxygen, in particular of oxygen radicals or reactive oxygen species, more preferably by superoxide radicals, hydroxyl radicals, hypochlorite radicals, hydrogen peroxide, various lipid peroxides, peroxy radical, alkoxy radical of lipids, hydroperoxide, ozone and hypochlorite anion, as well as excited oxygen molecules (singlet oxygen). Such radicals and substances may be formed inter alia by radiation, preferably by X-radiation or other ionizing radiation, e.g. α-, β- and γ-radiation, more preferably the radiation may exhibit a wave length of 10 nm to 10 pm. Moreover, such radicals and substances may be formed by acetaldehyde or by consumption of alcohol.

In a preferred embodiment the composition according to the present invention is combined with any medicament. The composition according to the present invention may be administrated or taken at the same time, prior or after the administration of the medicament.

In a preferred embodiment the composition according to the present invention is used within the context of a radiation therapy for tumour patients. In a preferred embodiment the composition according to the present invention may be administered three days before, 4 days after or three days before and 4 days after irradiation of the subject. Preferably the composition may be administered in a 24 hours interval.

In a preferred embodiment the composition according to the present invention is used within the context of a chemotherapy for tumour patients. The composition of the present invention may be administrated in combination with a medicament used in chemotherapy. In a preferred embodiment the composition of the present invention may be administrated or taken in combination with a medicament used in chemotherapy, wherein the composition of the present invention is administrated or taken at the same time, prior or after the medicament for chemotherapy.

The composition according to the present invention may be administered or taken prior, during or after a radiation therapy or chemotherapy for tumour patients.

In a further embodiment the composition of the present invention can also be used as a medicament, food supplement and/or dietary supplement.

A further embodiment refers to the composition of the present invention for use in the treatment and/or prevention of radical or harmful forms of oxygen derived diseases in general. A preferred embodiment refers to the composition of the present invention for use in the treatment and/or prevention of oxygen radical or reactive oxygen species derived diseases. A further embodiment refers to the composition of the present invention for use in the treatment and/or prevention of radiation-induced gastrointestinal syndrome. Symptoms of the radiation-induced syndrome are bleeding, diarrhea, temperature, spasms hypovolemia and lost of bowel mucosa. A further embodiment refers to the composition of the present invention for use in the treatment and/or prevention of anemia, in particular iron-deficiency anemia, ischemic reperfusion injury, inflammatory diseases, systemic lupus erythematosis, myocardial infarction, stroke, traumatic hemorrhage, spinal cord trauma, Crohn's disease, autoimmune diseases, e.g. rheumatoid arthritis and diabetes, cataract formation, uveitis, emphysema, gastric ulcers, oxygen toxicity, neoplasia, radiation sickness, cancer, Alzheimer's disease, Parkinson's disease, hemochromatosis, deafness, atherosclerosis, psychosis, movement disorders, bone marrow failure, pancytopenia, fatal immune dysfunction and schizophrenia.

In a further aspect the present invention relates to a method of treating a disorder, disease or condition in a subject in need of treatment and/or prevention, which method comprises administering to said subject an effective amount of composition according to the present invention. In particular said method of treatment may be for the treatment and/or prevention of radical or harmful forms of oxygen derived diseases in general, in particular of oxygen radical or reactive oxygen species derived diseases. In a preferred embodiment said method of treatment may be for the treatment and/or prevention of the diseases and disorders listed above.

The dosage and route of administration used in a method of treatment or prevention according to the present invention depends on the specific disease or disorder to be treated. The route of administration may be for example oral, topical, nasopharyngeal, parenteral, intravenous, rectal or any other route of administration.

Excessive amounts of free radicals, in particular of oxygen radicals or reactive oxygen species can lead to cell injury and death, which results in many diseases such as stroke, cancer, diabetes and major disorders. Many forms of cancer are thought to be the result of reactions between free radicals, in particular of oxygen radicals or reactive oxygen species and DNA, resulting in mutations that can adversely affect the cell cycle and potentially lead to malignancy.

The amount of free radicals, in particular oxygen radicals or reactive oxygen species may be enhanced in subjects during diagnostic radiology or in case of radiation therapy in connection with tumor diseases. Consequently, radiologists, dentists, radiological assistances and workers in plants for X-ray tubes and nuclear power may exhibit higher amounts of free radicals, in particular of oxygen radicals or reactive oxygen species. Moreover, also personnel in airplanes and spacecrafts are exposed to radiation and thus, may exhibit higher amounts of free radicals, in particular of oxygen radicals or reactive oxygen species. And the same holds true for mountaineers. There is also overwhelming evidence that there is a causative role of smoking-generated oxygen free radicals (huge oxidative stress load) in the pathogenesis of many chronic degenerative diseases, e.g. emphysema, lung cancer, coronary artery diseases.

Radicals produced e.g. by radiolysis of water by radiation, e.g. X-rays, $\alpha$-, $\beta$- and $\gamma$-radiation damages e.g. DNA causing mutation of the DNA which may lead to the development of divers diseases, e.g. tumors. Moreover, radicals cause or promote damages, such as degeneration, atrophy, fibrosis or necrosis of tissues.

In a further embodiment, the composition of the present invention is used in the prevention of aging. Organisms age because cells accumulate free radical, in particular oxygen radical or reactive oxygen species damage over time. Free radical, in particular oxygen radical or reactive oxygen species damage within cells has been linked to a range of disorders including anemia, in particular iron-deficiency anemia, cancer, arthritis, atherosclerosis, Alzheimer's disease, and diabetes. Free radical chemistry is an important aspect of phagocytosis, inflammation, and apoptosis. Cell suicide, or apoptosis, is the body's way of controlling cell death and involves free radicals, in particular oxygen radical or reactive oxygen species. Such degenerative diseases associated with aging may be caused by radicals, in particular by oxygen radicals or reactive oxygen species.

A further embodiment refers to the composition according to the present invention for use as a food supplement or dietary supplement. Food supplements and dietary supplements may be concentrated sources of nutrients or other substances with a nutritional or physiological effect whose purpose is to supplement the normal diet.

The food supplement or dietary supplement taken orally may supplement the diet. The dietary supplement or food supplement may be provided as a tablet, capsule, dragee, pill, powder, suppository, or any other galenic formulation. Dietary supplements and food supplements may also be provided in bars, drinks, shakes and other food products. In general, a dietary supplement is not intended to be the sole item of a meal or diet. Dietary supplements and food supplements may be taken before, after or simultaneously with a meal. Dietary supplements and food supplements may be taken once or several times a day. Dietary supplements and food supplements may be taken at any time of day. The following examples explain the present invention but are not considered to be limiting.

Primary goal of this study was the investigation of changes in X-irradiated biomolecules in the absence and presence of the composition according to the present invention and various other additives, to address the following problems: Alleged protective efficiency of the additives during and after irradiation (elucidation of primary and secondary damages) and their repair capability.

EXAMPLE 1

Preparation of the Supplement Solution

The Supplement Consists of the Following Ingredients:

| | |
|---|---|
| Coenzyme Q10* | 100 mg (CoQ10P40 250 mg) |
| Riboflavin | 40 mg (riboflavin 40 mg equivalent) |
| L-Cystine | 500 mg |
| Niacin | 20 mg |
| Ascorbic acid | 940 mg |
| Succinic acid | 100 mg |
| Fumaric acid | 100 mg |
| L-Glutamine | 950 mg |

Ingredients of the supplement except Coenzyme Q10 were purchased from Sigma Aldrich Japan (Tokyo, Japan). *CoQ10P40 (Nisshin Pharma, Tokyo Japan) was used as Coenzyme Q 10. CoQ10P40 contains 40% weight of Coenzyme Q10.

EXAMPLE 2

Activity Test of Lysozyme

The activity test of lysozyme was taken as efficient test system.

The enzyme lysozyme was chosen, because lysozyme is a well-characterized protein, both from the biochemical, physico-chemical, crystallographic and radiobiological point of view. Moreover, lysozyme is an example of a self-defence system against bacterial infections in the body. Structure and function of unirradiated and irradiated lysozyme have been characterized in detail. As follows from previously published papers any other protein could be used as well, with gradual differences caused by the characteristics (e.g., amino acid composition, 3D structure) of the protein selected. This behavior can be attributed to the fact that the principles of the interaction of ionizing radiation and biomolecules are governed by the oxidizing action of ROS, on the one hand, and the scavenging ability of antioxidants, on the other, irrespective of the biomolecule(s) in its neighbourhood. If a scavenger is able to protect a protein, it will also be able to protect any other molecules, e.g. DNA, lipid, membrane, etc., depending on the extent of solubility of the antioxidant applied.

The hen's egg white lysozyme was purchased from Serva (Heidelberg, Germany), additives and all other substances were of the highest available grade. Lysozyme (0.1 mg/ml) and the additives (10 mM, except otherwise stated) were dissolved in dilute, air-saturated 1 mM sodium phosphate buffer pH 6.5 and were irradiated at 25° C. with X-rays (0-1 kGy) in the absence or presence of the additives. Activity tests of the lysozyme were performed as described in Shugar, 1952. The measurement of lysozyme activity and the ultraviolet inactivation of lysozyme. Biochim. Biophys. Acta 8, 302-309. were recorded in a Jasco UV/VIS spectrophotometer V-530.

The activity test of lysozyme is simple and straightforward. The method described by Shugar uses the diluted unirradiated or irradiated enzyme and a cell suspension of *Micrococcus lysodeikticus* in a special activity buffer (66 mM sodium phosphate buffer with 17 mM NaCl, pH 7.0). The bacterium is suspended in an Erlenmeyer flask in the activity buffer at a concentration of 0.2 mg/ml. Before using the bacterial suspension in the test, the flask has to be swivelled to ensure homogeneous pipetting into the cuvette. Working briskly, the enzyme sample was pipetted to the bacterial solution, and using parafilm to tightly seal the cuvette, was homogeneously hand-mixed. Typical test mixtures (total of 3 ml) consisted of 2.98 ml bacterial solution plus 0.02 ml unirradiated enzyme sample in the absence or presence of additives, and 2.95 ml bacterial solution plus 0.05 ml irradiated enzyme (250 Gy) in the absence of additives, and 2.6 ml bacterial solution plus 0.4 ml irradiated enzyme (1000 Gy) in the absence of additives, to allow reasonable handling of the samples. The decrease in absorbance resulting from a breakdown of the bacteria by the enzyme is measured in a 3-ml cuvette in a spectrophotometer at a wavelength of 450 nm for a continuous time period of 3 min at 25° C.

Different decreases in absorbance reflect different activities. The test may also be applied for lysozyme in the presence of antioxidants, since, owing to the high dilution of the samples (lysozyme+antioxidants) in the test and the wavelength used, the antioxidants will not disturb the results of the activity measurement. No further separation techniques are needed.

Irradiations were performed in small 2-ml plastic cups at 25° C. The dosage measurement of X-rays was obtained by Fricke dosimetry (ferrous sulfate dosimetry).

EXAMPLE 3

Activity of Lysozyme Irradiated after Application of Tested Additives

In the present experiment the lysozyme was mixed with the following additives: composition of example 1, ascorbic acid (10 mM), glutathione (10 mM), thiourea (10 mM), sodium-formate (10 mM) or mannitol (10 mM). Afterwards the lysozyme-additive mixture was irradiated with X-rays of an energy dose of 500 Gy and 1000 Gy, respectively. Additionally, the lysozyme was irradiated with X-rays of energy doses of 250, 500, 750 and 1000 Gy without the presence of any additives.

Afterwards the irradiated lysozyme was used in the activity assay as described in example 2 to determine the activity of the lysozyme. For comparison, activities are given in percent. The native, unirradiated lysozyme is used as reference and is considered to have 100% activity.

Table 1 shows the results of experiments with irradiated lysozyme (c=0.1 mg/ml) in the absence or presence of different additives added before irradiation and at different X-ray doses.

X-irradiation in the absence of additives results in a nearly complete loss of activity, if the dose applied is sufficient high (1000 Gy). Irradiation at lower doses yields less pronounced damages. The presence of the composition as described in example 1 exhibits a strong protection against X-irradiation. At lower doses applied, the protection is more pronounced.

The decrease in the activity of lysozyme correlates with the occurrence of radicals produced by radiolysis due to the irradiation. The application of the composition as described in example 1 acts as a scavenger and thus, leads to protection of the lysozyme indicated by high activity of the lysozyme.

TABLE 1

Influence of additives on the activity of irradiated lysozyme

| Irradiation | a.r. Additive (final conc.) | % Activity |
| --- | --- | --- |
| None | None | 100 (reference) |
| X (250 Gy) | None | 13 |
| X (500 Gy) | None | 1.5 |
| X (500 Gy) | S 1:7 dilution (=1 mg/ml) | 89 |
| X (750 Gy) | None | 0.3 |
| X (1000 Gy) | None | 0.1 |
| X (1000 Gy) | S 1:7 dilution (=1 mg/ml) | 73 |
| X (1000 Gy) | Ascorbic acid (10 mM) | 90 |
| X (1000 Gy) | Glutathione (10 mM) | 58 |
| X (1000 Gy) | Thiourea (10 mM) | 90 |
| X (1000 Gy) | Sodium-Formate (10 mM) | 75 |
| X (1000 Gy) | Mannitol (10 mM) | 51 |

S = composition as described in example 1,
a.r. = ante radiationem = before irradiation,
gray (Gy) represents the amount of radiation required to deposit 1 joule of energy in 1 kilogram of any kind of matter.

EXAMPLE 4

Activity of Lysozyme Irradiated after Application of the Composition in Variable Concentrations In the present experiment the lysozyme was mixed with the composition of example 1 of various concentrations. Afterwards the lysozyme-additive mixture was irradiated with X-rays of an energy dose of 250 Gy. Additionally, the lysozyme was irradiated with X-rays of an energy dose of 250 Gy without the presence of any additives.

Afterwards the irradiated lysozyme was used in the activity assay as described in example 2 to determine the activity of the lysozyme, wherein the determination of the lysozyme activity was repeated 24 h after irradiation. For comparison, activities are given in percent. The native, unirradiated lysozyme is used as reference and is considered to have 100% activity.

Table 2 summarizes the results for X-irradiated lysozyme (c=0.1 mg/ml) using variable concentrations of the composition described in example 1. For this purpose, a dose of 250 Gy was applied, to allow the registration of more accurate results than at 1000 Gy. In the absence of the composition, an inactivation takes place, which is further intensified in the post-irradiation phase (monitoring 24 h after irradiation).

All concentrations of the composition (even a dilution of 1:10000) deliver a protection of the lysozyme during irradiation and against further inactivation during storage for 24 h. The most pronounced effects are obtained when using the highest composition concentrations.

The decrease in the activity of lysozyme correlates with the occurrence of radicals produced by radiolysis due to the irradiation. The application of the composition as described in example 1 acts as a scavenger and thus, leads to protection of the lysozyme indicated by high activity of the lysozyme.

TABLE 2

Influence of the composition on the activity of irradiated lysozyme

| Irradiation | a.r. Additive (final conc.) | % Activity | % Activity (24 h) |
|---|---|---|---|
| None | None | 100 (reference) | 93 (slight inactivation) |
| X (250 Gy) | None | 18 (strong inactivation) | 14 (further inactivation) |
| None | S undiluted (=7 mg/ml) | 107 (slight repair) | 105 |
| X (250 Gy) | S undiluted (=7 mg/ml) | 96 | 94 |
| X (250 Gy) | S 1:10 dilution (=0.7 mg/ml) | 86 | 85 |
| X (250 Gy) | S 1:100 dilution (=0.07 mg/ml) | 64 | 54 (further inactivation) |
| X (250 Gy) | S 1:1000 dilution (=0.007 mg/ml) | 32 | 26 (further inactivation) |
| X (250 Gy) | S 1:10000 dilution (=0.0007 mg/ml) | 22 | 18 (further inactivation) |

S = composition as described in example 1,
a.r = ante radiationem = before irradiation,
gray (Gy) represents the amount of radiation required to deposit 1 joule of energy in 1 kilogram of any kind of matter.

EXAMPLE 5

Activity of Lysozyme Irradiated Prior to Application of the Composition in Variable Concentrations In the present experiment the lysozyme was first irradiated with X-rays of an energy dose of 250 Gy. Afterwards the lysozyme was mixed with the composition of example 1 in a 1:2 or 1:10 dilution. Additionally, the lysozyme was irradiated with X-rays of an energy dose of 250 Gy without the presence of any additives.

Afterwards the irradiated lysozyme was used in the activity assay as described in example 2 to determine the activity of the lysozyme, wherein the determination of the lysozyme activity was repeated 24 h after irradiation. For comparison, activities are given in percent. The native, unirradiated lysozyme is used as reference and is considered to have 100% activity.

Table 3 presents the results for lysozyme (c=0.1 mg/ml) X-irradiated in the absence of the composition of example 1, but furnished with this composition after irradiation. Activity measurements were performed 24 h after irradiation and addition of the composition. The results prove a protection by the composition against inactivation during storage (24 h) and a significant repair behaviour.

The decrease in the activity of lysozyme correlates with the occurrence of radicals produced by radiolysis due to the irradiation. The application of the composition as described in example 1 acts as a scavenger and leads to a repair of the lysozyme indicated by high activity of the lysozyme.

TABLE 3

Repair of the lysozyme activity by application of the compositon

| Irradiation | p.r. Additive (final conc.) | % Activity | % Activity (24 h at RT) |
|---|---|---|---|
| None | None | 100 (reference) | 93 (slight inactivation) |
| X (250 Gy) | None | 18 (strong inactivation) | 14 (further inactivation) |
| X (250 Gy) | S 1:2 dilution (=3.5 mg/ml) | 25 (repair) | |
| X (250 Gy) | S 1:10 dilution (=0.7 mg/ml) | 20 (repair) | |

S = composition described in example 1,
p.r. = post radiationem = after irradiation,
gray (Gy) represents the amount of radiation required to deposit 1 joule of energy in 1 kilogram of any kind of matter.

EXAMPLE 6

Preparation of the Supplement Solution

The Supplement Consists of the Following Ingredients:

| | |
|---|---|
| Coenzyme Q10* | 100 mg (CoQ10P40 250 mg) |
| Riboflavin | 40 mg (riboflavin 40 mg equivalent) |
| L-Cystine | 500 mg |
| Niacin | 20 mg |
| Ascorbic acid | 940 mg |
| Succinic acid | 100 mg |
| Fumaric acid | 100 mg |
| L-Glutamine | 950 mg |

Ingredients of the supplement except Coenzyme Q10 were purchased from Sigma Aldrich Japan (Tokyo, Japan). *CoQ10P40 (Nisshin Pharma, Tokyo Japan) was used as Coenzyme Q 10. CoQ10P40 contains 40% weight of Coenzyme Q10.

The above listed single components were mixed with 50 ml water and then 84 mg sodium bicarbonate was added to adjust the pH and for solubility reasons of cystine. This solution was afterwards diluted to 0.6 mg/µl and 0.3 mg/µl.

EXAMPLE 7

Hydrogen Peroxide Levels in the Blood of Mice Pretreated with the Composition of the Invention or Vitamin C after Irradiation Mice:

For the following experiments C57BL/6 mice (21 gram body weight) were purchased from Japan SLC (Shizuoka, Japan). The mice were used for the experiments with an age of 8 weeks.

In this Experiment Six Groups were Built, Wherein Each Group Comprises 6 Mice:
  a) the first group of mice were not treated and built the negative control,
  b) the second group of mice built the positive control, thus the mice were treated with 6 Gy radiation and 72 hours after irradiation blood sampling was performed,
  c) the third group of mice was treated with 150 mg Vitamin C per kg body weight,
  d) the forth group of mice was treated with 15 mg Vitamin C per kg body weight, and e) the fifth group of mice was treated with 15 mg of the composition in Example 6 per kg body weight.

The following experiment was performed for the first, second and fifth group in three independent experiments, for the third group in two independent experiments and for the forth group in one experiment.

Each mouse was placed in a well-ventilated acrylic container. The composition in Example 6 and Vitamin C, respectively suspended in 0.5 ml water was orally administered three times in a 24 hours interval to the mice of the third to fifth group. 24 hours after the third administration mice were exposed to 6 Gy whole body irradiation (WBI), given at a dose rate of 0.45 Gy/min at 150 kV and 5 mA (HITACHI MBR-1505R2, Tokyo, Japan). The beam was filtered through a 2 mm aluminum board. 72 hours after irradiation blood sampling was performed.

Measurement of Free Radicals in the Blood Samples:

The d-ROMs (Reactive Oxygen Metabolites) test by using Free Carpe Diem photometric analytical system (Diacron, Grosseto, Italy) was used for the measurement of free radical metabolites in the blood samples of the mice. It is a spectrophotometric method that assesses overall oxidative stress by measuring total hydroperoxide levels, given that hydroperoxides are intermediate oxidative products of lipids, peptides, and amino acids. Briefly, 0.02 ml plasma was diluted in 1 ml acetate-buffered solution. Hydroperoxide groups react with the transition metal ions liberated from the proteins in the acidic medium, and are converted to alkoxyl and peroxyl radicals according to the Fenton reaction. These newly formed radicals, the quantities of which are directly proportional to those of the peroxides, were trapped chemically with 0.02 ml chromogen (N, N-diethyl-para-phenylendiamine), leading to the formation of the radical cation of this chromogen. The purple color resulting from this reaction over time was monitored in a spectrophotometer (Wismarll FRAS4, Tokyo, Japan) at 505 nm. The results of this method were expressed in µmol per liter.

TABLE 4

Hydrogen peroxide concentration in blood of mice after pre-treatment and irradiation

|  | Hydrogen peroxide concentration [µmol/l] |
|---|---|
| Effect of radiation 6Gy |  |
| Positive Control | 144.6 |
| Negative Control | 124.9 |
| Difference | 19.7 |
| Reduction rate | 100% |
| Effects of Vitamin C 150 mg/kg |  |
| Positive Control | 144.7 |
| Vitamin C 150 mg/kg | 140.5 |
| Difference | 3.8 |
| Reduction rate | 19.29% |
| Effects of Composition of Example 6 15 mg/kg |  |
| Positive Control | 144.7 |
| Composition of Example 6 15 mg/kg | 135 |
| Difference | 9.7 |
| Reduction rate | 49.24% |
| Effects of Vitamin C 15 mg/kg |  |
| Positive Control | 144.7 |
| Vitamin C 15 mg/kg | 149.6 |
| Difference | 5.1 |
| Increase rate | 25.89% |

The increase in hydrogen peroxide concentration in the blood sample of mice due to irradiation at 6 Gy compared to negative control represented by hydrogen peroxide concentration in the blood of untreated mice was 19.7 µmol/l. If the mice were pre-treated with 150 mg Vitamin C per kg body weight three times in a 24 hours interval before irradiation, the concentration of hydrogen peroxide was decreased by 3.8 µmol/l, thus the reduction rate is 19.29%, in case of pre-treatment with 15 mg of the composition in Example 6 per kg body weight the concentration of hydrogen peroxide was decreased by 9.7 µmol/l, thus the reduction rate is 49.24%. In contrast the pre-treatment with 15 mg Vitamin C per kg body weight resulted in an increase of the concentration of hydrogen peroxide by 5.1 µmol/l, thus the increase rate is 25.89%.

Thus, this experiment shows that the administration of the composition according to the present invention prior to irradiation reduces the level of free radicals, namely hydrogen peroxide causing cell damages and radical-derived diseases.

EXAMPLE 8

Preparation of the Composition According to the Invention

Following mixture was put in water and shake well till all ingredients are complete soluble.

|  | Wt (mg) |
|---|---|
| Coenzyme Q10 | 100 |
| Ascorbic acid | 940 |
| L-Cystine | 500 |
| L-Glutamine | 850 |
| Fumaric acid | 100 |
| Succinic acid | 100 |
| Niacin | 20 |
| Sodium bicarbonate | 84 |

Then Riboflavin sodium phosphate (for injection) 2 ml (40 mg) was mixed.

The final solution contains the following ingredients.

|  | Wt (mg) |
|---|---|
| Coenzyme Q10 | 100 |
| Ascorbic acid | 940 |
| L-Cystine | 500 |
| L-Glutamine | 850 |
| Fumaric acid | 100 |
| Succinic acid | 100 |
| Niacin | 20 |
| Riboflavin | 40 |
| Total | 2650 |

EXAMPLE 9

Effect of the Composition of Example 8 on the Hydrogen Peroxide Blood Level in Mice Using Various Concentrations of the Composition Mice:

For the following experiments C57BL/6 mice (21 gram body weight) were purchased from Japan SLC (Shizuoka, Japan). The mice were used for the experiments with an age of 8 weeks.

In this Experiment Eight Groups were Built:

a) the first group of mice built the positive control comprising 5 mice, thus the mice were treated with 6 Gy radiation and 72 hours after irradiation blood sampling was performed, b) the second group of mice built the negative control comprising 5 mice, thus the mice were untreated, b) the third to eighth group of mice was treated with 5, 10, 15, 20, 25 or 30 mg of the composition of Example 8 per kg body weight. The third to sixth group comprise each 10 mice, the seventh group eight mice and the eighth group comprises six mice.

Each mouse was placed in a well-ventilated acrylic container. The composition in Example 8 was orally administered three times in a 24 hours interval to the mice of the third to eighth group in the respective concentration, i.e. 5, 10, 15, 20, 25 or 30 mg composition per kg body weight. 24 hours after the third administration mice were exposed to 6 Gy whole body irradiation (WBI), given at a dose rate of 0.45 Gy/min at 150 kV and 5 mA (HITACHI MBR-1505R2, Tokyo, Japan). The beam was filtered through a 2 mm aluminum board. 72 hours after irradiation blood sampling was performed.

Measurement of Free Radicals in the Blood Samples:

The d-ROMs (Reactive Oxygen Metabolites) test by using Free Carpe Diem photometric analytical system (Diacron, Grosseto, Italy) was used for the measurement of free radical metabolites in the blood samples of the mice as described in Example 7 above.

TABLE 5

Hydrogen peroxide concentration in blood of mice after pre-treatment with various concentrations of composition according to Example 8 and irradiation

| | Hydrogen peroxide concentration [μmol/l] |
|---|---|
| Effect of radiation 6Gy | |
| Positive Control | 147.4 |
| Negative Control | 115.6 |
| Difference | 31.8 |
| Reduction rate | 100.00% |
| Effects of Composition 5 mg/kg body weight of Example 8 | |
| Positive Control | 147.4 |
| Composition of Example 8 5 mg/kg | 128.5 |
| Difference | 18.9 |
| Reduction rate | 59.43% |
| Effects of Composition of Example 8 10 mg/kg body weight | |
| Positive Control | 147.4 |
| Composition of Example 8 10 mg/kg | 126.9 |
| Difference | 20.5 |
| Reduction rate | 64.47% |
| Effects of Composition of Example 8 15 mg/kg body weight | |
| Positive Control | 147.4 |
| Composition of Example 8 15 mg/kg | 122.5 |
| Difference | 24.9 |
| Reduction rate | 78.30% |
| Effects of Composition of Example 8 20 mg/kg body weight | |
| Positive Control | 147.4 |
| Composition of Example 8 20 mg/kg | 124.9 |

TABLE 5-continued

Hydrogen peroxide concentration in blood of mice after pre-treatment with various concentrations of composition according to Example 8 and irradiation

| | Hydrogen peroxide concentration [μmol/l] |
|---|---|
| Difference | 22.5 |
| Reduction rate | 70.75% |
| Effects of Composition of Example 8 25 mg/kg body weight | |
| Positive Control | 147.4 |
| Composition of Example 8 25 mg/kg | 127.3 |
| Difference | 20.1 |
| Reduction rate | 63.21% |
| Effects of Composition of Example 8 30 mg/kg body weight | |
| Positive Control | 147.4 |
| Composition of Example 8 30 mg/kg | 142 |
| Difference | 5.4 |
| Reduction rate | 16.98% |

The increase in hydrogen peroxide concentration in the blood sample of mice due to irradiation at 6 Gy compared to negative control represented by hydrogen peroxide concentration in the blood of untreated mice was 31.8 μmol/l.

If the mice were pre-treated with 5 mg composition of Example 8 per kg body weight three times in a 24 hours interval before irradiation, the concentration of hydrogen peroxide was decreased by 18.9 μmol/l, thus the reduction rate is 59.43%, in case of pre-treatment with 10 mg of the composition in Example 8 per kg body weight the concentration of hydrogen peroxide was decreased by 20.5 μmol/l, thus the reduction rate is 64.47%. The highest reduction was achieved if the mice were pre-treated with 15 mg composition of Example 8 per kg body weight three times in a 24 hours interval before irradiation, the concentration of hydrogen peroxide was decreased by 24.9 μmol/l, thus the reduction rate is 78.3% and if the mice were pre-treated with 20 mg composition of Example 8 per kg body weight three times in a 24 hours interval before irradiation, the concentration of hydrogen peroxide was decreased by 22.5 μmol/l, thus the reduction rate is 70.75%. With increasing concentration of the composition of Example 8, i.e. 25 and 30 mg/kg body weight, the reduction in the hydrogen peroxide decreased, so that the reduction rate decreases to 63.21% and 16.98%, respectively.

Thus, this experiment shows that the administration of the composition according to the present invention prior to irradiation reduces the level of free radicals, namely hydrogen peroxide causing cell damages and radical-derived diseases.

EXAMPLE 10

Effects of the Composition of Example 8 on the Hydrogen Peroxide Blood Level of Mice Using Different Administration Forms and Duration Mice:

For the following experiments C57BL/6 mice (21 gram body weight) were purchased from Japan SLC (Shizuoka, Japan). The mice were used for the experiments with an age of 8 weeks.

In this Experiment Six Groups were Built:

a) the first group of mice comprising 27 mice, built the positive control, thus the mice were treated with 6 Gy radiation and 72 hours after irradiation blood sampling was performed, b) the second group of mice, comprising 28 mice, the third group of mice, comprising 12 mice and the forth group of mice, comprising 11 mice were treated with 15 mg of the composition according to Example 8 per kg body weight by oral administration, c) the fifth group of mice, comprising 12 mice, was treated with 15 mg of a composition similar to that of Example 8 containing cysteine instead of cystine per kg body weight by oral administration, and d) the sixth group of mice, comprising 12 mice, was treated with 15 mg of the composition according to Example 8 per kg body weight by intra-peritoneal administration.

Each mouse was placed in a well-ventilated acrylic container. The mice representing the positive control were exposed to 6 Gy whole body irradiation (WBI), given at a dose rate of 0.45 Gy/min at 150 kV and 5 mA (HITACHI MBR-1505R2, Tokyo, Japan). The beam was filtered through a 2 mm aluminum board. 72 hours after irradiation blood sampling was performed.

The composition in Example 8 was orally administered three times in a 24 hours interval to the mice of the second group in the concentration of 15 mg composition per kg body weight, i.e. the mice were pre-treated 3 days with the composition of Example 8 before irradiation. 24 hours after the third administration mice were irradiated using conditions as for positive control. 72 hours after irradiation blood sampling was performed.

The composition in Example 8 was orally administered four times in a 24 hours interval to the mice of the third group starting 24 hours after irradiation using same conditions as for positive control and blood sampling was performed 24 hours after last oral administration. The mice of the third group were post-treated 4 days with the composition of Example 8 after irradiation.

The mice of forth group were treated three times in a 24 hours interval with 15 mg/kg composition of Example 8 before irradiation using same conditions as for positive control and four times in a 24 hours interval starting 24 hours after irradiation and blood sampling was performed 24 hours after last oral administration. The mice of the forth group were pre-treated 3 days with the composition of Example 8 before irradiation and post-treated 4 days with this composition after irradiation.

The mice of fifth group were treated with a composition similar to that of Example 8, wherein L-cystine was replaced by L-cysteine. This composition in a concentration of 15 mg/kg body weight was orally administrated three times in a 24 hours interval to the mice of the fifth group. 24 hours after the third administration mice were irradiated using same conditions as for positive control and blood sampling was performed 72 hours after irradiation.

The mice of fifth group were treated analogous to the mice of second group, except that the composition was administered intra-peritoneal.

Measurement of Free Radicals in the Blood Samples:

The d-ROMs (Reactive Oxygen Metabolites) test by using Free Carpe Diem photometric analytical system (Diacron, Grosseto, Italy) was used for the measurement of free radical metabolites in the blood samples of the mice as described in Example above.

TABLE 6

Hydrogen peroxide concentration in blood of mice

| | Hydrogen peroxide concentration [μmol/l] |
|---|---|
| Effect of radiation 6Gy | |
| Positive Control | 146 |
| Negative Control | 126.38 |
| Difference | 19.62 |
| Reduction rate | 100% |
| Effects of Composition 15 mg/kg body weight of Example 8 in 3 days pre-treatment (second group) | |
| Positive Control | 146 |
| Composition of Example 8 15 mg/kg | 133.03 |
| Difference | 12.97 |
| Reduction rate | 66.11% |
| Effects of Composition of Example 8 15 mg/kg body weight in 4 days post-treatment (third group) | |
| Positive Control | 146 |
| Composition of Example 8 15 mg/kg | 129.9 |
| Difference | 16.1 |
| Reduction rate | 82.06% |
| Effects of Composition of Example 8 15 mg/kg body weight in 3 days pre-treatment and 4 days post-treatment (forth group) | |
| Positive Control | 146 |
| Composition of Example 8 15 mg/kg | 123.5 |
| Difference | 22.5 |
| Reduction rate | 114.68% |
| Effects of Composition variant with cysteine 15 mg/kg body weight of Example 8 in 3 days pre-treatment (fifth group) | |
| Positive Control | 146 |
| Composition of Example 8 15 mg/kg | 124.6 |
| Difference | 21.4 |
| Reduction rate | 109.07% |
| Effects of Composition 15 mg/kg body weight of Example 8 in 3 days pre-treatment using intra-peritoneal administration (sixth group) | |
| Positive Control | 146 |
| Composition of Example 8 15 mg/kg | 122.3 |
| Difference | 23.7 |
| Reduction rate | 120.8% |

The increase in hydrogen peroxide concentration in the blood sample of mice due to irradiation at 6 Gy compared to negative control represented by hydrogen peroxide concentration in the blood of untreated mice was 19.62 μmol/l. If the mice were pre-treated with 15 mg of the composition of Example 8 per kg body weight three times in a 24 hours interval before irradiation, the concentration of hydrogen peroxide was decreased by 12.97 μmol/l, thus the reduction rate is 66.11%, in case of post-treatment with 15 mg of the composition in Example 8 per kg body weight the concentration of hydrogen peroxide was decreased by 16.01 μmol/l, thus the reduction rate is 82.08%. The pre-treatment of 3 days and post-treatment of 4 days with 15 mg/kg of the composition of Example 8 leads to a decrease in the concentration of hydrogen peroxide by 22.5 μmol/l, thus a reduction rate of 114.86%. The pre-treatment with the Composition according to Example 8, except that cystine is replaced by cysteine leads to a decrease in the concentration of hydrogen peroxide by 21.4 μmol/l, thus a reduction rate of 109.07%. Moreover, the intra-peritoneal administration of the composition of Example 8 leads to a higher reduction in the concentration of hydrogen peroxide by 23.7 µmol/l compared to the oral administration (see second group), thus the reduction rate is 120.8%.

EXAMPLE 11

Effect of the Composition of Example 8 on the Hydrogen Peroxide Blood Level in Mice Treated with Ethanol Mice:

For the following experiments C57BL/6 mice (21 gram body weight) were purchased from Japan SLC (Shizuoka, Japan). The mice were used for the experiments with an age of 8 weeks.

In this Experiment Seven Groups were Built:
a) the first group of mice built the positive control comprising 14 mice, thus 7 g/kg body weight ethanol was administrated twice intra-peritoneal to the mice in a 24 hours interval and 24 hours after the second administration blood sampling was performed,
b) the second group of mice built the negative control comprising 4 mice, thus the mice were untreated,
c) the third to seventh group of mice was treated with 10, 15, 20, 25 or 30 mg of the composition of Example 8 per kg body weight. The third group comprises 9 mice, the forth group 15 mice, the fifth and sixth group 8 mice and the seventh group comprises 10 mice.

Each mouse was placed in a well-ventilated acrylic container. The composition in Example 8 was orally administered five times in a 24 hours interval to the mice of the third to sixth group in the respective concentration, i.e. 10, 15, 20, 25 or 30 mg composition per kg body weight. 7 g/kg body weight ethanol was injected intra-peritoneal on day 4 and 5 one hour after the treatment with the composition of Example 8. 24 hours after final treatment with composition of Example 8 blood sampling was performed.

Measurement of Free Radicals in the Blood Samples:

The d-ROMs (Reactive Oxygen Metabolites) test by using Free Carpe Diem photometric analytical system (Diacron, Grosseto, Italy) was used for the measurement of free radical metabolites in the blood samples of the mice as described in Example 7 above.

TABLE 7

Hydrogen peroxide concentration in blood of mice

| | Hydrogen peroxide concentration [µmol/l] |
|---|---|
| Effect of Ethanol 7 g/kg | |
| Positive Control | 155.6 |
| Negative Control | 134 |
| Difference | 21.6 |
| Reduction rate | 100.00% |
| Effects of Composition of Example 8 10 mg/kg body weight | |
| Positive Control | 155.6 |
| Composition of Example 8 10 mg/kg | 139.3 |
| Difference | 16.3 |
| Reduction rate | 75.46% |
| Effects of Composition of Example 8 15 mg/kg body weight | |
| Positive Control | 155.6 |
| Composition of Example 8 15 mg/kg | 138.1 |
| Difference | 17.5 |
| Reduction rate | 81.02% |
| Effects of Composition of Example 8 20 mg/kg body weight | |
| Positive Control | 155.6 |
| Composition of Example 8 20 mg/kg | 138.25 |
| Difference | 17.35 |
| Reduction rate | 80.32% |
| Effects of Composition of Example 8 25 mg/kg body weight | |
| Positive Control | 155.6 |
| Composition of Example 8 25 mg/kg | 138.75 |
| Difference | 16.85 |
| Reduction rate | 78.01% |
| Effects of Composition of Example 8 30 mg/kg body weight | |
| Positive Control | 155.6 |
| Composition of Example 8 30 mg/kg | 139.5 |
| Difference | 16.1 |
| Reduction rate | 74.54% |

The increase in hydrogen peroxide concentration in the blood sample of mice due to injection of ethanol compared to negative control represented by hydrogen peroxide concentration in the blood of untreated mice was 21.6 µmol/l.

If the mice were pre-treated with 10 mg of the composition in Example 8 per kg body weight the concentration of hydrogen peroxide was decreased by 16.3 µmol/l, thus the reduction rate is 75.46%. The highest reduction was achieved if the mice were pre-treated with 15 mg composition of Example 8 per kg body weight five times in a 24 hours interval, the concentration of hydrogen peroxide was decreased by 17.5 µmol/l, thus the reduction rate is 81.02% and if the mice were pre-treated with 20 mg composition of Example 8 per kg body weight three times in a 24 hours interval, the concentration of hydrogen peroxide was decreased by 17.35 µmol/l, thus the reduction rate is 80.32%. With increasing concentration of the composition of Example 8, i.e. 25 and 30 mg/kg body weight, the reduction in the hydrogen peroxide decreased, so that the reduction rate decreases to 78.01% and 74.54%, respectively.

The invention claimed is:

1. A method for the treatment and/or prevention of radicals and harmful forms of oxygen in a human or animal, or the treatment and/or prevention of a disease in a human or animal, said disease selected from radiation-induced gastrointestinal syndrome, anemia, ischemic reperfusion injury, inflammatory diseases, systemic lupus erythematosis, myocardial infarction, stroke traumatic hemorrhage, spinal cord trauma, Crohn's disease, rheumatoid arthritis, cataract formation, uveitis, emphysema, gastric ulcers, oxygen toxicity, neoplasia, radiation sickness, cancer, Alzheimer's disease, Parkinson's disease, hemochromatosis, deafness, atherosclerosis, psychosis, bone marrow failure, pancytopenia, fatal immune dysfunction, movement disorders and schizophrenia, comprising administering to said subject from 10 to 20 mg of a composition per kilogram of body weight of said subject comprising 3 to 5 mass % coenzyme Q10, 1 to 2 mass % riboflavin, 15 to 20 mass % L-cystine or L-cysteine, 0.5 to 1.0 mass % niacin, 28 to 43 mass % Vitamin C, 3 to 5 mass % succinic acid, 3 to 5 mass % fumaric acid and 27 to 42 mass % L-glutamine.

2. The method of claim 1, wherein the composition is administered in a concentration of 15 mg per kilogram of body weight of said subject.

3. The method of claim 2, wherein the composition comprises 35.47 mass % Vitamin C, 32.08 mass % L-glutamine, 18.88 mass % L-cystine or L-cysteine, 1.51 mass % riboflavin, 3.77 mass % succinic acid, 3.77 mass % fumaric acid, 3.77 mass % coenzyme Q10, and 0.75 mass % niacin.

4. The method of claim 3, wherein the composition is in a liquid form or in the form of a capsule, dragee, pill, powder, suppository, or any other galenic formulation.

5. The method of claim 2, wherein the composition is in a liquid form or in the form of a capsule, dragee, pill, powder, suppository, or any other galenic formulation.

6. The method of claim 1, wherein the composition comprises 35.47 mass % Vitamin C, 32.08 mass % L-glutamine, 18.88 mass % L-cystine or L-cysteine, 1.51 mass % riboflavin, 3.77 mass % succinic acid, 3.77 mass % fumaric acid, 3.77 mass % coenzyme Q10, and 0.75 mass % niacin.

7. The method of claim 6, wherein the composition is in a liquid form or in the form of a capsule, dragee, pill, powder, suppository, or any other galenic formulation.

8. The method of claim 1, wherein the composition is in a liquid form or in the form of a capsule, dragee, pill, powder, suppository, or any other galenic formulation.

* * * * *